(12) United States Patent
Garito et al.

(10) Patent No.: US 7,935,110 B1
(45) Date of Patent: May 3, 2011

(54) EYELID RF SURGERY

(75) Inventors: Jon C. Garito, Oceanside, NY (US);
Alan G. Ellman, Oceanside, NY (US)

(73) Assignee: Ellman International, Inc., Oceanside, NY (US)

( * ) Notice: Subject to any disclaimer, the term of this patent is extended or adjusted under 35 U.S.C. 154(b) by 981 days.

(21) Appl. No.: 11/821,431

(22) Filed: Jun. 25, 2007

(51) Int. Cl.
*A61B 18/14* (2006.01)
*A61N 1/06* (2006.01)

(52) U.S. Cl. .......................... 606/41; 607/99
(58) Field of Classification Search ............ 606/41; 607/99
See application file for complete search history.

(56) References Cited

U.S. PATENT DOCUMENTS

| 4,517,975 | A | * | 5/1985 | Garito et al. | 606/41 |
| 5,766,171 | A | * | 6/1998 | Silvestrini | 606/49 |
| 6,068,628 | A | * | 5/2000 | Fanton et al. | 606/41 |
| 6,395,001 | B1 | * | 5/2002 | Ellman et al. | 606/41 |
| 6,432,105 | B1 | * | 8/2002 | Ellman et al. | 606/48 |
| 6,920,883 | B2 | * | 7/2005 | Bessette et al. | 606/41 |

* cited by examiner

*Primary Examiner* — Lee S Cohen

(57) ABSTRACT

A procedure employing non-ablative radio-frequency energy for improving the appearance of eyelids or the performance of eyelid blepharoplasty, and the monopolar electrode used in the procedure. The electrode is specially configured to provide a reasonably uniform electric field distribution at the skin surface when applied transconjunctivally on the inner surfaces of the upper or lower lids being treated. Preferably, the active end of the electrode forms a generally rectangular upward-facing platform. While RF electrosurgical currents are applied to the electrode, the platform surface is moved back and forth across and in contact with the tissue.

9 Claims, 2 Drawing Sheets

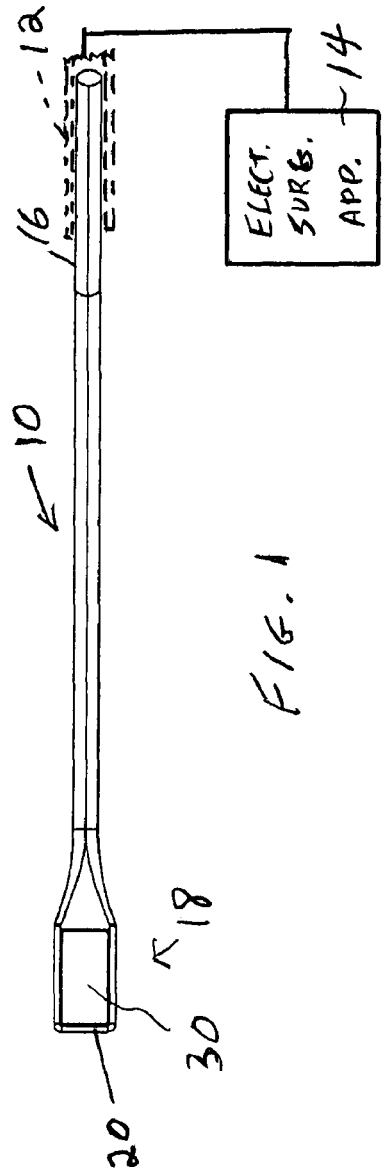
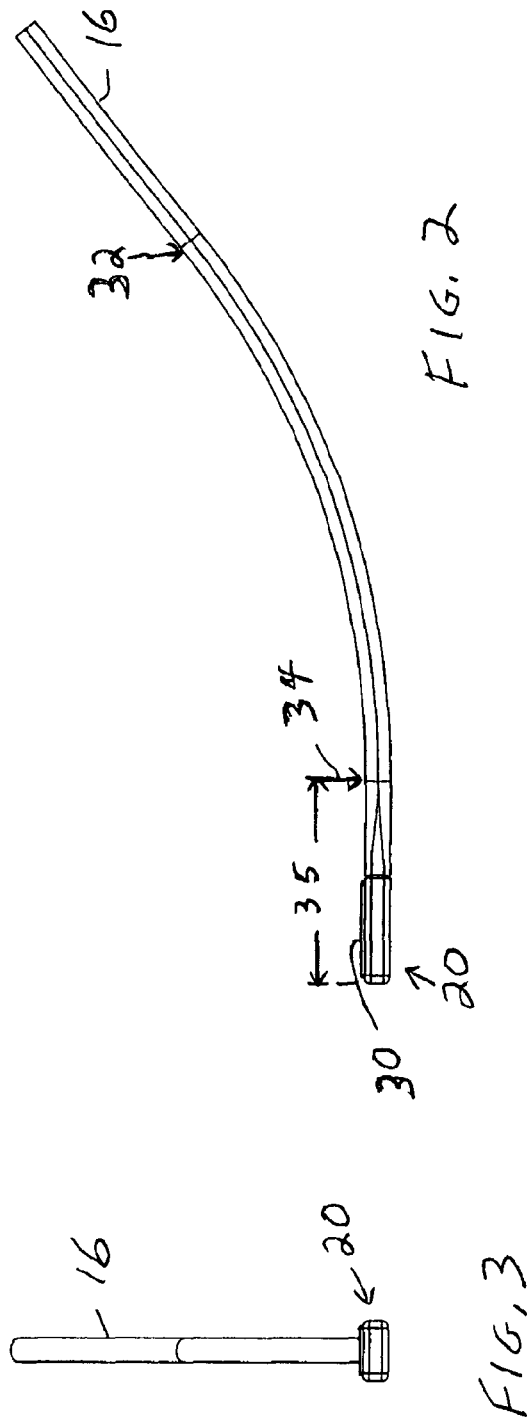

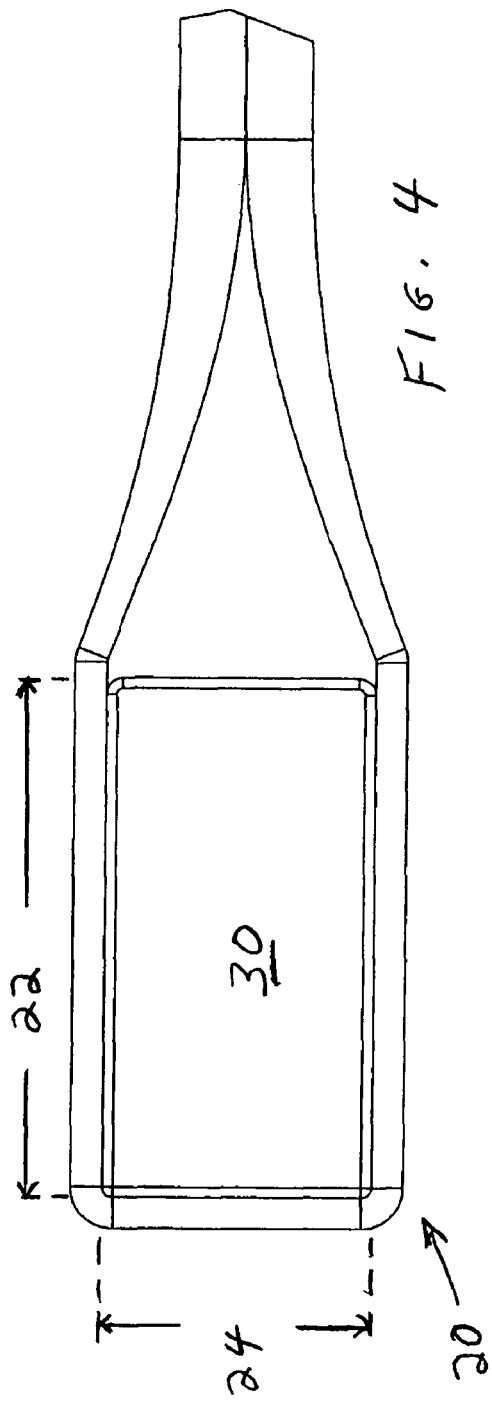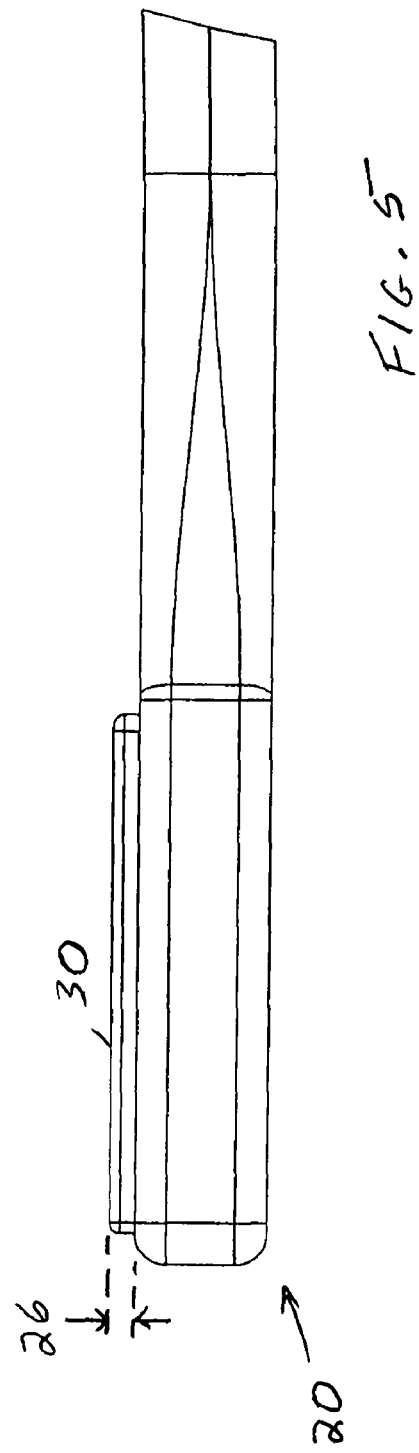

EYELID RF SURGERY

RELATED APPLICATION

Copending US application, Ser. No. 11/655,720, filed Jan. 22, 2007.

This invention relates to a procedure for cosmetically treating skin tissue using non-ablative radio-frequency (RF) energy. It also relates to a monopolar electrode for use in such procedures.

BACKGROUND OF THE INVENTION

The related application Ser. No. 11/655,720, the contents of which are herein incorporated by reference, describes a non-ablative electrosurgical procedure for treating skin lesions or blemishes using a monopolar electrode that is specially configured to provide a small-area, reasonably uniform electric field distribution at the skin surface being treated. Preferably, the active end of the electrode is flat and blunt. The flat blunt active electrode end is applied to the skin lesion or blemish, while RF electrosurgical currents are applied to the electrode, in an up and down tapping motion in such manner that contact between the skin and the active electrode end is intermittent. Preferably, after a small number of skin taps with the electrode end, the tapped area is wiped with a wet gauze or cloth, and the procedure of intermittent tapping with the RF electrode interrupted with wet wipes is continued until the blemish disappears.

Blepharoplasty is both a functional or cosmetic surgical procedure intended to reshape the upper eyelid or lower eyelid by the removal and/or repositioning of excess tissue as well as by reinforcement of surrounding muscles and tendons. Lower eyelid blepharoplasty is almost always done for cosmetic reasons, to improve puffy lower eyelid "bags" and reduce the wrinkling of skin. Blepharoplasty is typically performed through external incisions made along the natural skin lines of the eyelids, such as below the lashes of the lower lids, or from the inside surface of the upper or lower eyelid. Initial swelling and bruising take one to two weeks to resolve and at least several months are needed until the final result becomes stable.

SUMMARY OF THE INVENTION

An object of the present invention is to employ non-ablative radio-frequency energy for improving the appearance of eyelids or the performance of eyelid blepharoplasty.

In accordance with a feature of the invention, a monopolar electrode is used that is specially configured to provide a reasonably uniform electric field distribution at the skin surface when applied transconjunctivally on the inner surfaces of the upper or lower lids being treated. Preferably, the active end of the electrode forms a generally rectangular upward-facing platform. Preferably, the platform surface is planar, but it can also have a small rounded convex curvature.

In accordance with a further feature of the invention, the surface platform active electrode end extends at the distal end of an elongated curved shank whose proximal end is mounted in a conventional electrosurgical handpiece. The overall shape of the electrode is configured to enable the surgeon to readily apply the active end of the electrode inside the upper or lower lid surface being treated, while RF electrosurgical currents are applied to the electrode, for the purpose of tightening and rejuvenating the lower lid skin through the transconjunctival approach. The RF surgery is non-ablative, and can be used alone or following a standard blepharoplasty procedure after suturing to further tighten the skin.

Preferably, the electrode platform is bio-compatible and of a highly conductive material, which also contributes to low skin temperatures. Noble metals are preferred for the composition of the electrode end.

It is also preferred that not only is the power setting of the radio-frequency-generating instrument set low, but also the cut/coag mode is selected. In the cut/coag mode, the radio-frequency waveform at a preferred frequency in the 3.8-4 MHz range is fully rectified before being supplied to the electrode.

It is believed that radiofrequency technology produces an electric current that generates heat through resistance in the dermis and subcutaneous tissue. The thermal effect depends on the conductivity features of the treated tissue. Non-ablative RF treatment has a lower risk of complications, shorter recovery time and less disruption of regular activities.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described preferred embodiments of the invention, like reference numerals designating the same or similar elements.

BRIEF DESCRIPTION OF THE DRAWINGS

In the drawings:

FIG. 1 is a top plan view of one form of a monopolar electrode according to the invention shown connected to electrosurgical apparatus;

FIG. 2 is an side view of the electrode of FIG. 1;

FIG. 3 is an end view of the electrode of FIG. 1;

FIG. 4 is an enlarged top view of the active end of the electrode of FIG. 1;

FIG. 5 is an enlarged side view of the active end of the electrode of FIG. 1.

DETAILED DESCRIPTION OF PREFERRED EMBODIMENTS

In the present application, FIG. 1 is a top view of one form of electrosurgical electrode 10 of the invention shown connected by way of a conventional handpiece 12 (in dashed lines) to a radio-frequency generating instrument 14. The monopolar electrode 10 is mounted to the handpiece 12 in the usual way by way of a bare metal shank end 16. The handpiece may have a conventional front end adapted to receive and hold rigidly the conductive shank end 16 of the metal electrode 10 comprising a proximate portion at the shank end 16 and a distal portion 18 which contains the active end of the electrode. Except for the shank end 16 in the handpiece which is uncoated, most of the remaining part of the electrode is coated with an insulating coating which is very thin and is not visible. The distal end portion 18 is also coated except for a platform section 20 comprising a generally rectangular bare metal member with length 22 and width dimensions 24 (FIGS. 4 and 5) and a height 26, which constitutes the working end mainly the planar surface 30. The handpiece is electrically-insulating or if conductive is covered with an electrically-insulating coating. The electrode 10 is configured for easy manipulation so that the active surface 30 can be applied by the surgeon to the inner surface of the upper or lower lid. For the embodiment illustrated, as an example, the radius of the gently curved section located between the arrows designated 32 and 34 is about 38°, preferably between about 30-45°, and the length (not designated) is about 2.6 inches, preferably about 2.2-3.0 inches, long enough to be applied by a surgeon such that the bare flat surface 30 over its whole planar area can be pressed and gently moved back and forth along the skin on the inside surface of the eyelid. The portion of the electrode designated 35 is about 0.5 inches long.

While the uncoated portion of the entire electrode 10 is preferably made of solid metal, it is also possible that only the working end 20 is made of a highly conductive metal such as a noble metal welded or brazed to the conductive metal. The remainder of the electrode can be made of the usual metals such as brass or tungsten or stainless steel. The working end should preferably also be bio-compatible. The high conductivity property assists in producing low tissue temperatures on the skin and also minimizes sticking.

The preferred electrode should have a range of lengths 22 from about 0.18 to 0.30 inches, preferably about 0.25 inches, a range of widths 24 from about 0.11 to 0.14 inches, preferably about 0.13 inches, and a range of heights from about 0.01 to 0.02 inches, preferably about 0.012 inches. These dimensions are important to ensure that the active platform end can easily fit under the eyelid and yet leave sufficient clearance that it can be moved back and forth applying gentle pressure to the tissue while the electrosurgical apparatus is energized to heat the tissue to a temperature where collagen can shrink, but not so hot as to cause injury to the tissue.

The RF electrode in accordance with the invention together with the method of using the electrode by applying it on its platform side posteriorly to the eyelid tissue offers many important advantages to the cosmetic surgeon and aesthetician.

RF electrosurgical currents have minimal to no lateral heat spread. The electrode is insulated except for a platform region that is active. It is applied on the posterior surface of the skin. When activated through the RF apparatus a heating action is produced that begins to tighten the skin tissue. The heating action penetrates the collagen and causes it to contract improving tone and texture. In addition new collagen grows to further tighten the skin. The electrode of the invention and the RF technology is a safe way to tighten and smoothen the skin transconjunctivally as a stand-alone procedure. In addition, as collagen is in the dennis and subcutaneous layers, through a subcutaneous approach the cosmetic result of lower lid blepharoplasty can be improved so the post approach following transconjunctival blepharoplasty is even safer with the electrode of the invention than applying the RF energy alone on the surface of the skin.

In addition, the surgeon can perform a blepharoplasty with incision and excision in a bloodless field with a cutting electrosurgical electrode, and without changing the surgical handpiece device, can switch the apparatus from generating the filtered current waveform for cutting to the full or partially rectified current waveform for non-ablative surgery and replace the cutting electrode with that of the invention, to safely tighten the skin following the completion of the surgery.

In this description, by "axial" is meant parallel to the long axis of the electrode (horizontal in FIG. 1). By "lateral" is meant transverse to the long axis of the electrode. When referring to the position of the platform surface 30, assuming that the electrode 10 is positioned as shown in FIG. 2, then the electrode lies in a vertical plane (of the drawing of FIG. 2) and "upward facing" shall mean in the upward direction in FIG. 2 lateral to the platform surface 30. "Generally flat" in reference to the platform surface 30 shall mean that the surface is planar or has a slightly convex shape.

Other usable mechanical or electrical structures following the teachings of this application will be appreciated by those skilled in this art. As with the embodiments of the prior application, the insulating coating will prevent accidental touching of patient tissue by the electrode sides, so that the discharge is localized to the region adjacent the bare surface 30.

The radio-frequency apparatus 14 preferably outputs high frequency (RF) radio-frequency currents in the range of about 3.8-4.0 MHz. The use of 3.8-4.0 MHz radio-frequency currents at low powers with a monopolar electrode with the flat or slightly curved surface applied intermittently as it moves over the tissue maintains the surface below a harmful temperature to avoid burning. Examples of suitable radio-frequency generating apparatus are the Model SURGITRON Dual-Frequency and IEC radio-frequency units manufactured by and available from Ellman International, Inc. of Oceanside, N.Y.

In summary, the electrode of the invention in conjunction with RF technology is a safe way to tighten and smoothen the skin through a subcutaneous approach improving therefore the cosmetic result especially of lower lid blepharoplasty. This procedure is believed to be an effective, non-invasive, economical and safe tool. In addition, costs connected to this new method are rather low.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. A surgical procedure intended to reshape the upper eyelid or lower eyelid for improving the appearance of skin tissue of a patient, comprising the steps:
   A. providing:
      (a) an electrode in the form of an elongated first member having a first end and a distal second end being the active end of the electrode,
      (b) the first end being adapted for receiving a radio-frequency voltage capable of generating radio-frequency currents at the second end,
      (c) the second end having a generally flat bare surface configured to form a platform surface extending approximately lateral to the first member, the platform surface being rectangular and planar, the platform surface having a range of lengths from about 0.18 to 0.30 inches, a range of widths from about 0.11 to 0.14 inches, and a range of heights from about 0.01 to 0.02 inches,
   B. providing a radio-frequency generating instrument for supplying radio-frequency currents in the megacycle range to the electrode when activated;
   C. connecting the first end of the electrode to the radio-frequency generating instrument;
   D. applying the platform surface of the electrode to the patient's inside surface of the upper eyelid or lower eyelid to be treated and continuously moving the platform surface of the electrode back and forth while in contact with the inside eyelid surface such that radio-frequency currents are applied to the patient's tissue in contact with the platform surface while the radio-frequency generating instrument is activated to improve the appearance of the eyelid being treated.

2. A procedure as claimed in claim 1, further comprising the step of:
   E. adjusting the radio-frequency generating instrument to generate a rectified current waveform.

3. A procedure as claimed in claim 2, wherein steps A-D are carried out following an eyelid blepharoplasty.

4. A procedure as claimed in claim 1, wherein the radio-frequency currents are at a frequency of about 3.8-4 MHz.

5. A procedure as claimed in claim 4, wherein the electrode has a curved shape.

6. An electrode for use in a surgical procedure intended to reshape the upper eyelid or lower eyelid for improving the appearance of skin tissue of a patient, comprising:
   (a) an elongated member having a first end and a distal second end being the active end of the electrode,
   (b) the first end being adapted for receiving a radio-frequency voltage capable of generating radio-frequency currents at the second end,
   (c) the second end having a generally flat bare surface configured to form a platform surface extending approximately lateral to the first member,
   (d) the electrode being monopolar,
   (e) the platform surface being planar and generally rectangular with a length, width and height,
   (f) wherein the platform surface has a range of lengths from about 0.18 to 0.30 inches, a range of widths from about 0.11 to 0.14 inches, and a range of heights from about 0.01 to 0.02 inches.

7. An electrode as claimed in claim 6, wherein only the platform surface is electrically-conductive, the remainder of the second end being electrically-insulated.

8. An electrode as claimed in claim 6, wherein the elongated member has a curved shape with the platform surface extending along the inside of the curve, the curved shape lying in a vertical plane.

9. An electrode for use in a surgical procedure intended to reshape the upper eyelid or lower eyelid for improving the appearance of skin tissue of a patient, comprising:
   (a) an elongated member having a first end and a distal second end being the active end of the electrode,
   (b) the first end being adapted for receiving a radio-frequency voltage capable of generating radio-frequency currents at the second end,
   (c) the second end having a generally flat bare surface configured to form a platform surface extending approximately lateral to the first member,
   (d) the electrode being monopolar,
   (e) the platform surface being planar and generally rectangular with a length, width and height,
   (f) wherein the platform surface has a length of about 0.25 inches, a width of about 0.13 inches, and a height of about 0.012 inches.

* * * * *